US008105635B2

(12) United States Patent
Hayson et al.

(10) Patent No.: US 8,105,635 B2
(45) Date of Patent: Jan. 31, 2012

(54) POST-IMPREGNATION TREATMENTS TO IMPROVE DISTRIBUTION OF METAL BIOCIDES IN AN IMPREGNATED SUBSTRATE

(75) Inventors: Kimberly S. Hayson, Redhouse, WV (US); William C. Hoffman, Dunbar, WV (US); Albert F. Joseph, Charleston, WV (US); Brian T. Keen, Pinch, WV (US)

(73) Assignee: Union Carbide Chemicals & Plastics Technology LLC, Midland, MI (US)

( * ) Notice: Subject to any disclaimer, the term of this patent is extended or adjusted under 35 U.S.C. 154(b) by 349 days.

(21) Appl. No.: 12/381,466

(22) Filed: Mar. 12, 2009

(65) Prior Publication Data

US 2010/0016426 A1    Jan. 21, 2010

Related U.S. Application Data

(60) Provisional application No. 61/135,121, filed on Jul. 17, 2008.

(51) Int. Cl.
*A01N 59/20* (2006.01)
*A01N 59/16* (2006.01)
*A61K 33/24* (2006.01)
*A61K 33/34* (2006.01)
*A61K 31/74* (2006.01)
*A61K 51/00* (2006.01)
*A61M 36/14* (2006.01)
*B05D 3/02* (2006.01)

(52) U.S. Cl. .............. 424/630; 424/1.61; 424/78.09; 424/617; 424/632; 424/633; 424/634; 424/638; 427/393; 427/397; 514/499; 514/500

(58) Field of Classification Search ............ 424/1.61, 424/78.09, 406, 617, 630, 632, 633, 634, 424/638; 514/499, 500; 427/393, 397
See application file for complete search history.

(56) References Cited

U.S. PATENT DOCUMENTS

| | | | |
|---|---|---|---|
| 4,567,115 A | 1/1986 | Trumble | |
| 4,847,002 A | 7/1989 | Trumble et al. | |
| 4,929,454 A | 5/1990 | Findlay et al. | |
| 5,304,237 A | 4/1994 | Barth et al. | |
| 5,342,438 A | 8/1994 | West | |
| 5,395,656 A | 3/1995 | Liang | |
| 5,460,751 A | 10/1995 | Ma et al. | |
| 5,635,217 A | 6/1997 | Goettsche et al. | |
| 5,846,305 A | 12/1998 | Payzant | |
| 5,853,766 A | 12/1998 | Goettsche et al. | |
| 5,874,025 A | 2/1999 | Heuer et al. | |
| 6,110,263 A | 8/2000 | Goettsche et al. | |
| 6,395,698 B1 | 5/2002 | Daun et al. | |
| 6,428,902 B1 | 8/2002 | Amundson et al. | |
| 6,489,037 B1 | 12/2002 | Winterowd et al. | |
| 2003/0077219 A1 | 4/2003 | Ploss et al. | |
| 2004/0258767 A1 | 12/2004 | Leach et al. | |
| 2004/0258768 A1 | 12/2004 | Richardson et al. | |
| 2004/0258838 A1 | 12/2004 | Richardson et al. | |
| 2005/0118280 A1 | 6/2005 | Leach et al. | |
| 2005/0249812 A1 | 11/2005 | Leach et al. | |
| 2005/0256026 A1 | 11/2005 | Hodge et al. | |
| 2005/0265893 A1 | 12/2005 | Leach et al. | |
| 2006/0078686 A1 | 4/2006 | Hodge et al. | |
| 2006/0086284 A1 | 4/2006 | Zhang et al. | |
| 2006/0112850 A1 | 6/2006 | Zhang et al. | |
| 2006/0147632 A1 | 7/2006 | Zhang et al. | |
| 2006/0162611 A1 | 7/2006 | Richardson et al. | |
| 2009/0258943 A1 | 10/2009 | Keen et al. | |

FOREIGN PATENT DOCUMENTS

| | | |
|---|---|---|
| AU | B-15517/92 | 10/1992 |
| DE | 243665 | 11/1987 |
| EP | 0381482 A2 | 8/1990 |
| EP | 0514644 | 11/1992 |
| EP | 0641633 | 3/1995 |
| EP | 0739698 | 4/1995 |
| EP | 0682091 | 11/1995 |
| EP | 0747182 | 12/1996 |
| WO | WO 98/39146 | 9/1998 |
| WO | WO 02/47876 | 6/2002 |
| WO | WO 2004/011215 | 2/2004 |

(Continued)

OTHER PUBLICATIONS

Heaton et al., "Studies on biocide release and performance of novel anti-fungal paints," 1991, Biofouling: The Journal of Bioadhesion and Biofilm Research, vol. 3, Issue 1, pp. 35-43 (Abstract only available; attached).*

(Continued)

*Primary Examiner* — Johann Richter
*Assistant Examiner* — Jane C Oswecki
(74) *Attorney, Agent, or Firm* — Kagan Binder PLLC

(57) ABSTRACT

The present invention relates to post-treatment compositions and methods useful for modifying the distribution of metal biocide(s) in biodegradable substrates such as wood, other cellulosic products, starch-based products, and the like that are vulnerable to decay due to insects, fungi, microbes, and the like. The compositions include complexing agents of moderate strength that are able to facilitate mobilization and redistribution of metal biocide(s) in substrates without undue leaching. The compositions can be used, for example, to redistribute the metal biocide(s) into depleted regions of a substrate by redistribution of metal biocide from other regions of the substrate. Post-treatment compositions that include additional metal biocide can also replenish these regions with the freshly supplied, additional biocide. Thus, the depleted regions can be restored by redistribution and/or replenishment mechanisms. Service life of substrates in the field benefits by these post-treatments as a consequence.

21 Claims, No Drawings

FOREIGN PATENT DOCUMENTS

| | | |
|---|---|---|
| WO | WO 2005007368 | 1/2005 |
| WO | WO 2006044225 | 4/2006 |
| WO | WO 2006053284 | 5/2006 |
| WO | WO 2006/072659 | 7/2006 |
| WO | WO 2007/133220 | 11/2007 |
| WO | WO 2008/013981 | 1/2008 |
| WO | WO 2009/078945 A2 | 6/2009 |

OTHER PUBLICATIONS

Material Safety Data Sheet, ProWood ACQ Pressure Treated Wood, 4 pages, May 15, 2002.

Townsend, T.G. et al., "Environmental Impacts of Treated Wood," Taylor & Francis Group, Boca Raton, 2006.

* cited by examiner

POST-IMPREGNATION TREATMENTS TO IMPROVE DISTRIBUTION OF METAL BIOCIDES IN AN IMPREGNATED SUBSTRATE

PRIORITY

The present non-provisional patent application claims benefit from U.S. Provisional Patent Application having Ser. No. 61/135,121, filed on Jul. 17, 2008, by Hayson et al. and titled POST-IMPREGNATION TREATMENTS TO IMPROVE DISTRIBUTION OF METAL BIOCIDES IN AN IMPREGNATED SUBSTRATE, wherein the entirety of said provisional patent application is incorporated herein by reference for all purposes.

FIELD OF THE INVENTION

The present invention relates to post-treatment compositions and methods useful for modifying the distribution of metal biocide(s) in biodegradable substrates such as wood, other cellulosic products, starch-based products, and the like that are vulnerable to decay due to insects, fungi, microbes, and the like. The compositions include complexing agents of moderate strength that are able to facilitate mobilization and redistribution of metal biocide(s) in substrates without undue leaching.

BACKGROUND OF THE INVENTION

Substrates such as wood, starch-based, and other biodegradable products used in interior or exterior applications can be vulnerable to attack by insects, fungi, microbes, and the like. To prevent decay that tends to result from these attacks, such substrates may be treated with preservatives to protect against decay and increase longevity. Historically, one widely used preservative composition is known by the CCA designation. This designation stands for chromated copper arsenate. CCA compositions were widely used to treat wood products, e.g., Southern Yellow Pine, used for decks, fencing, landscape timbers, and the like.

CCA compositions provide excellent protection against decay. However, relatively recently, health and safety concerns have been raised concerning the arsenic and chromium content of these compositions. Consequently, regulatory guidelines caused CCA usage for residential applications to stop on Jan. 1, 2004. As a result, the industry has developed and continues to develop new preservatives as substitutes for CCA compositions. Uncovering effective substitutes that are chromium and arsenic free has been challenging.

One newer class of copper-based preservatives uses a form of complexed copper that is water-soluble. The resultant solutions are considered homogeneous in the sense that the solutions are a single, liquid phase as applied to substrates. In many embodiments, the copper is complexed with complexing agents such as an alkanolamine. Examples of preservatives that contain copper complexes include copper polyaspartic acid, alkaline copper quaternary ammonium salt (also referred to in the industry by terminology such as "alkaline copper quat" or "ACQ"), copper azole, copper boron azole, ammoniacal copper citrate, copper bis(dimethyldithiocarbamate), and copper ethanolamine carbonate. Commonly, all these have a nitrogen base that complexes copper and carbonate ions to stabilize the resultant complex. Preservative compositions incorporating copper complexed with alkanolamine are referred to by the designation copper-amine. Copper-amine compositions currently dominate the preservative market for residential lumber applications.

As a positive, homogeneous preservative solutions tend to uniformly and thoroughly penetrate substrates. Unfortunately, as compared to biodegradable products treated with CCA materials, biodegradable products treated with these newer copper complex-based materials suffer higher copper losses in the field. Due to the water solubility of the complexes, the copper tends to leach more readily from the treated biodegradable products when exposed to rain or other water. The expectation that copper losses will occur due to leaching causes treatments to be made with larger amounts of copper to accommodate these expected losses. This is costly and wasteful. Also, copper solutions tend to be relatively sensitive to pH changes inasmuch as the soluble complexes can precipitate if the pH is too low. This limits formulation flexibility to the use of only alkaline complexing agents, for instance.

Heterogeneous preservative compositions also have been recently developed. In these, the metal biocide has been present in insoluble, particulate form dispersed in a liquid carrier. This dispersion, emulsion, or the like is then used to treat biodegradable substrates. Examples of heterogeneous preservative compositions in the form of dispersions of micronized copper containing particles are described, for example, in U.S. Pat. Publication Nos. 2004/0258767; 2005/0118280; 2005/0249812; 2005/0265893; 2006/0086284; 2006/0112850; and 2006/0147632.

As a positive, the copper containing particles in heterogeneous treatment compositions exhibit excellent retention characteristics and are highly resistant to leaching as compared to soluble, complexed copper. Unfortunately, the insoluble particles tend to reside only in the pores or other interstitial vacancies of substrates and penetrate poorly into cells or the like. This is believed to result in much less bioefficacy than could be obtained by more thorough and uniform substrate penetration. Heterogeneous strategies also suffer from particle size constraints, inasmuch as the effectiveness of the treatment can be compromised if the particles are too large or too small.

Thus, neither heterogeneous or homogeneous treatment strategies are wholly satisfactory. Homogeneous strategies have good bioefficacy, at least initially, but tend to leach too much. In the field leaching tends to occur most rapidly from surface regions of a substrate. This leaching causes these surface regions to become depleted with respect to metal biocide and, hence, more vulnerable to biodegradation. This limits the service life of substrates protected using conventional homogeneous treatment strategies. It would be desirable to prevent this depletion and/or to be able to replenish depleted regions in a practical and economical manner.

Heterogeneous strategies have good metal biocide retention, but tend to have less bioefficacy than is desired. In particular, the distribution of metal biocide particles tends to be highly nonuniform. Many regions are not protected very well at all, leaving these regions vulnerable to biodegradation. It would be desirable to find a way to improve the distribution and penetration of metal biocide(s) incorporated into substrates via heterogeneous compositions.

SUMMARY OF THE INVENTION

The present invention relates to post-treatment compositions and methods useful for modifying the distribution of metal biocide(s) in biodegradable substrates such as wood, other cellulosic products, starch-based products, and the like that are vulnerable to decay due to insects, fungi, microbes, and the like. The compositions include complexing agents of moderate strength that are able to facilitate mobilization and redistribution of metal biocide in substrates without causing undue leaching. The compositions can be used, for example, to replenish the bioprotection in depleted regions of a substrate by redistribution of metal biocide from other regions of the substrate. The compositions also can be used to more thoroughly and uniformly redistribute metal biocide impregnated into substrates via heterogeneous treatment compositions. Service life of substrates in the field can be vastly extended by these post-treatments.

In one aspect, the present invention relates to a method of replenishing a metal biocide content in a depleted region of an in-service, biodegradable substrate by redistributing a portion of a metal biocide from at least one other region of the substrate to the depleted region. The method includes contacting a surface of the substrate with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase. In preferred embodiments, said complexing agent and metal biocide have a complex stability constant $K_1$ in the range of from about 2.5 to about 6.5.

In another aspect, the present invention relates to a method of treating a biodegradable substrate. The biodegradable substrate is provided and includes (i) a first substrate region distal from a surface of the substrate, said first substrate region having a first concentration of a metal biocide; and (ii) a second substrate region proximal to the surface of the substrate, said second substrate region having a second concentration of metal biocide that is reduced relative to the first substrate region. The surface of the substrate is contacted with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase. In preferred embodiments, said complexing agent and metal biocide have a complex stability constant $K_1$ in the range of from about 2.5 to about 6.5, said contact causing a portion of the metal biocide in the first substrate region to be redistributed to the second substrate region.

In another aspect, the present invention relates to a method of treating a biodegradable substrate to modify a distribution of a metal biocide already incorporated into the substrate. The substrate is provided, said substrate comprising a distribution of a metal biocide. The substrate is contacted with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase. In preferred embodiments, said complexing agent and metal biocide have a complex stability constant $K_1$ in the range of from about 2.5 to about 6.5, said contact causing the distribution of the metal biocide in the substrate to be modified.

In another aspect, the present invention relates to a multi-step treatment for distributing a metal biocide in a biodegradable substrate. A metal biocide is incorporated into the biodegradable substrate. The substrate is contacted with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase. In preferred embodiments, said complexing agent and metal biocide have a complex stability constant $K_1$ in the range of from about 2.5 to about 6.5, said contact causing the distribution of the metal biocide in the substrate to be modified.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides post-treatment strategies that may be used to modify or otherwise enhance the distribution of metal biocides in a biodegradable substrate incorporating one or more metal biocides. The terminology "post-treatment" in the context of the present invention means that the treatment strategies of the invention are generally applied to biodegradable substrates that already incorporate metal biocides(s) from one or more prior impregnation treatments.

The post-treatment strategies can modify or otherwise enhance the distribution and/or retention of metal biocide in a biodegradable substrate in a variety of ways. The post-treatment strategies are particularly useful when the distribution of metal biocide in the substrate is less uniform than might be desired. In a typical situation, different substrate regions may have different loadings or concentrations of the metal biocide relative to other region(s). Some region(s) might be relatively lean in metal biocide, while other region(s) might be relatively rich in metal biocide. The present invention can be used to redistribute the metal biocide among these regions to make the distribution more uniform. In addition to such redistribution among substrate regions, the present invention can also be used to replenish depleted substrate regions by incorporating fresh, additional metal biocide into the substrate.

For example, conventional heterogeneous treatment compositions yield treated substrates in which the metal biocide tends to exist in chunks of insoluble particles residing in the pores or other interstitial vacancies of the substrate. Thus, the metal biocide generally exists where these particles are located, but not elsewhere. The treatment of the present invention can improve the distribution of the heterogeneous metal biocide at least to the extent and depth that the fluid composition of the invention is able to penetrate into the substrate.

The ability of the treatment to modify the distribution of the heterogeneous metal biocide can be observed visually by microscopic examination. After impregnation with a heterogeneous preservative composition, but prior to a post-treatment with a fluid composition of the present invention, the particles of metal biocide are easily viewed by visual inspection of a section of a treated wood sample. The surfaces of the sample themselves appear to be unmodified in any way (e.g., there is no color change from the native color). This indicates that the metal biocide exists mainly in the particles themselves with little if any penetration into wood cells. In contrast, after a post-treatment of the present invention, such large chunks of metal biocide particles are no longer visible. Instead, the substrate surfaces contacted by the treatment have a uniform color indicative of much more uniform and thorough penetration of the biocide into the cells of the substrate at least to the penetration depth of the post-treatment composition. To the extent any particles might still be visible, the particles are much finer. In practical effect, the post-treatment in this illustrative context causes the metal biocide in the particles to be redistributed from the pores or interstitial vacancies more deeply and thoroughly into the substrate. In the case of wood substrates, the redistribution facilitates deeper penetration into the wood cells themselves through the cell wall membranes.

As another example, often the metal biocide content of the surface regions of treated substrates that are in-service may tend to become depleted during the service life of the substrate. This depletion may occur as metal biocide leaches due to exposure to rain or other water sources, for instance. Consequently, depletion causes the substrate to include one or more regions distal to the substrate surface(s) that are relatively rich in metal biocide where depletion has not occurred and one or more regions proximal to the substrate surface(s) that are relatively lean in metal biocide due to depletion. In other words, the concentration of metal biocide near the substrate surface(s) becomes reduced relative to deeper regions of the substrate. At some point, sufficient metal biocide is lost near the surface such that these surface regions become more vulnerable to biodegradation than might be desired.

It certainly would be desirable to restore the metal biocide content, and hence restore the bioprotection, in these depleted regions. Unfortunately, apart from the biocide content that leaches to cause the depletion, the metal biocide in an in-service substrate tends to become fixed and is not readily mobile within the substrate. Due to this fixation, the metal biocide generally by itself will not redistribute itself sufficiently in the field to restore depleted regions adequately. Further, once the substrate is incorporated into a structure in the field, it generally is not physically or economically practical to dismantle the structure so that the substrate can be brought back to the substrate manufacturer and re-impregnated under factory conditions. The service life of the substrate is limited if the depletion is not reduced, avoided, and/or reversed.

Advantageously, the present invention offers an easy technical solution to this problem. With a simple treatment that is as easy as brushing, dipping, spraying or otherwise contacting the in-service substrate with a fluid composition of the invention, metal biocide from the relatively rich regions of the substrate will be redistributed to the depleted regions. If the treatment compositions include optional metal biocide, the depleted regions may also be replenished from the supply of fresh biocide added to the substrate from the treatment composition itself. Thus, the biocide content of depleted regions can be restored by both redistribution and/or replenishment mechanisms. Significantly, the treatment may occur under ordinary ambient conditions without resort to special pressure or vacuum conditions that might only be conveniently available under factory conditions. Even without using vacuum or pressure features available in the factory, the treatment composition penetrates sufficiently into the substrate to facilitate redistribution and/or replenishment of metal biocide near the surface regions. The compositions include ingredient(s) that then induce favorable mobilization and restoration of metal biocide in the depleted regions without undue leaching. The bioprotection restored to these regions helps to extend the service life of the substrate.

The present invention offers a paradigm shift when managing the service lives of structures built from treated substrates. In the past, the depletion phenomenon has limited the service life of these structures and/or required excessive treatment levels. Once the metal biocide near the surface is significantly depleted, the surface may tend to decay. The underlying portions now become exposed, and the cycle of depletion and decay continues. Ultimately, the structure is spent. In practical effect, the length of protection offered by one initial, single preservative treatment can govern the service life of these structures.

Substrate protection and service life is not so limited with the present invention. In representative modes of practice, substrates may be treated before depletion occurs to an undue degree or even earlier to avoid depletion. For instance, treatment may occur on a desired schedule. Upon treatment, the metal biocide content of the surface is restored, maintaining and/or restoring bioprotection. Significantly, service life is vastly extended through multiple treatment cycles, not just one.

A wide range of natural and synthetic biodegradable substrates in a wide range of applications may be beneficially post-treated using strategies of the present invention. Examples of cellulosic embodiments of biodegradable substrates include but are not limited to paper, cardboard, rope, veneer, lumber, manufactured timbers, cellulosic composites, engineered lumber, and sheet goods such as plywood, hardboard, particleboard, chipboard, fiberboard, strandboard, paneling, and the like. Representative end uses include residential, commercial, industrial, and marine interior or exterior applications such as construction lumber, trim, siding, decking, beams, railway sleepers, railroad ties, bridge components, jetties, wooden vehicles, docks, claddings, boxes, pallets, telephone poles, windows, doors, boats and ships, sheathing, foundation piles, posts, fences, marina structures, and other structures vulnerable to decay due to one or more of insects, fungi, microbes, and/or weathering.

Examples of metals that can be already present as metal biocide(s) in the substrates prior to a post-treatment of the present invention include one or more transition metal elements including the lanthanide and actinide series elements such as copper, strontium, barium, arsenic, antimony, bismuth, lead, gallium, indium, thallium, tin, zinc, chromium, cadmium, silver, gold, nickel, molybdenum, combinations of these, and the like. A preferred metal biocide is copper. Due to present regulatory requirements, it is desirable to limit or avoid the use of Cr and/or As in residential applications. Accordingly, some substrates to be post-treated in the practice of the present invention are desirably at least substantially arsenic free, at least substantially chromium free, and/or at least substantially chromium and arsenic free. However, it is appreciated that the principles of the present invention still would be useful to post-treat biodegradable substrates that include Cr and/or As from biodegradable substrates such as wood products.

The preservative compositions used to impregnate one or more metal biocides into biodegradable substrates may be heterogeneous or homogeneous compositions. Illustrative examples of homogeneous compositions include the ACQ preservative compositions. Assignee's co-pending U.S. Provisional Application having U.S. Ser. No. 61/007,614, filed Dec. 13, 2007, in the names of Kimberly S. Hayson, William C. Hoffman, Albert F. Joseph, Brian T. Keen for STRATEGIES FOR REDUCING LEACHING OF WATER-SOLUBLE METAL BIOCIDES FROM TREATED WOOD PRODUCTS and also describes many suitable embodiments. Others are described in U.S. Pat. No. 4,929,454. Additional, commercially available examples of homogeneous compositions are available under the trade designations NATUREWOOD (Osmose, Inc.) and PRESERVE (Chemical Specialties Inc.). Heterogeneous compositions have been described in U.S. Patent Pub. Nos. 2004/0258767; 2005/0118280; 2005/0249812; 2005/0265893; 2006/0086284; 2006/0112850; and 2006/0147632. The respective entireties of the patents and published patent applications cited above are incorporated herein by reference for all purposes.

In addition to one or more metal biocides, the preservative compositions impregnated into biodegradable substrates to be later post-treated as described herein may also include one or more other ingredients. For instance, the compositions may incorporate one or more complexing agents reactive with the metal biocide to form water-soluble metal complexes. In some embodiments, there is sufficient complexing agent in the preservative composition to form a water complex with substantially all, and more preferably all, of the metal biocide, yielding a homogeneous preservative composition. Representative examples of such homogeneous compositions are described in Assignee's co-pending U.S. Provisional Application having Ser. No. 61/007,614, filed Dec. 13, 2007, titled STRATEGIES FOR REDUCING LEACHING OF WATER-SOLUBLE METAL BIOCIDES FROM TREATED WOOD PRODUCTS, the entirety of which is incorporated herein by reference for all purposes.

In other embodiments, there may be a deficiency of complexing agent relative to the metal biocide in a preservative composition used to impregnate a biodegradable substrate prior to a post-treatment so that only a portion of the metal biocide is in the form of a soluble complex in the composition. At least a significant portion of the remainder of the metal biocide will be in the form of insoluble particles. Such preservative compositions are hybrid in the sense that these compositions include both soluble and insoluble metal biocide species. Hybrid preservative compositions are described in Assignee's co-pending United States Provisional Application filed Mar. 14, 2008, in the names of Brian T. Keen et al., titled HYBRID STRATEGIES FOR REDUCING LEACHING OF METAL BIOCIDES FROM BIODEGRADABLE SUBSTRATES, the entirety of which is incorporated herein by reference in its entirety for all purposes.

Metal biocides such as copper may not have as full a biocidal spectrum against microbes, fungi, pests, etc., as might be desired. Accordingly, one or more additional co-biocides may be incorporated into the preservative compositions in order to provide a fuller biocidal range. Additional co-biocides may include one or more of fungicidal, insecticidal, moldicidal, bactericidal, algaecidal biocides, and/or the like. These co-biocide(s) can be water soluble, partially water soluble, or water insoluble. If partially insoluble or insoluble, dispersants or chelating agents may be used to help disperse these in the preservative compositions. Thus, a wide range of inorganic and/or organic biocides may be used in accordance with conventional practices. Extensive lists of suitable biocides are provided in the patent literature, including in U.S. Pat. No. 5,874,025; and U.S. Pat. Pub. Nos. 2006/0086284, 2006/0162611, 2005/0256026, and 2005/0249812. The respective entireties of these patent documents are incorporated herein by reference for all purposes. Particularly preferred co-biocides include quaternary ammonium salts and the azole materials, including triazoles and imidazoles. Benzalkonium chloride or carbonate is one preferred quaternary ammonium salt; didecyldimethylammonium chloride or carbonate is another commonly used quaternary ammonium salt. Exemplary azoles include tebuconazole and propiconazole.

As another performance concern, a problem with soluble or easily dispersed forms of metal biocides is that these may tend to more readily leach from treated, biodegradable substrates when exposed to rain or other sources of water. Advantageously incorporating a leaching-reducing agent into the impregnation composition dramatically reduces such leaching. Particularly preferred leaching-reducing agents are described in Assignee's copending U.S. Provisional Application having U.S. Ser. No. 61/007,614, filed Dec. 13, 2007, in the names of Kimberly S. Hayson, William C. Hoffman, Albert F. Joseph, Brian T. Keen for STRATEGIES FOR REDUCING LEACHING OF WATER-SOLUBLE METAL BIOCIDES FROM TREATED WOOD PRODUCTS and the entirety of which application is incorporated herein by reference for all purposes. These leaching-reducing agents are described further below, as they are an optional ingredient that may be incorporated into post-treatment compositions of the present invention.

Other optional ingredients may also be beneficially used in the preservative compositions in accordance with conventional practices. For example, during the course of manufacture, if metal vessels may be used to prepare, transport, store, or otherwise contact the composition, the compositions may include a corrosion inhibitor. Boron containing inhibitors such as boric acid used in corrosion inhibiting amounts have been found to be suitable for this purpose. Other adjuvants include dispersants, emulsifiers, binders, fixatives, water repellants, coloring agents, antioxidants, ultraviolet stabilizers, emulsifiers, antistatic agents, dessicants; precipitation inhibitors; buffers; fire retardants; combinations of these, and the like used in accordance with conventional practices.

Post-treatment strategies of the present invention generally involve contacting the biodegradable substrate with an aqueous fluid composition, preferably a single phase composition, comprising a complexing agent capable of forming a water-soluble complex with at least one metal biocide in the substrate and/or in the fluid composition (if any biocide is present in the fluid composition as an optional ingredient). The treatment tends to modify the distribution of metal biocide within the substrate. In many embodiments, the distribution becomes more uniform. For example, in substrates that previously were impregnated with heterogeneous preservative compositions, relatively large chunks of metal biocide particles get dissolved and redistributed in the substrate more thoroughly and more uniformly at least in those regions into which the post-treatment composition penetrates into the substrate. For in-service substrates suffering from regions near the surface that are depleted with respect to metal biocide, the post-treatment can help restore the depleted regions by redistributing metal biocide from deeper portions of the substrate.

The complexing agent is also referred to as a ligand, chelant, chelating agent, or sequestering agent in the field of coordination chemistry. The complexing agent is desirably one that bonds to the central metal-containing species, often an ion, through one or more atoms of the complexing agent. These bonds may be a combination of one or more different kinds of bonds such as coordination and/or ionic bonds. An important aspect of the present invention involves using complexing agent(s) of moderate strength rather than one(s) that complex with the metal biocide too weakly or too strongly. If the complexing agent complexes too weakly with the metal biocide, the complexing agent might not be able to induce the desired mobilization and redistribution of the metal biocide within the substrate. On the other hand, if the complexing agent complexes too strongly, the resultant metal complex might be too soluble. This could lead to undue amounts of leaching of the metal biocide from the substrate rather than redistribution. Advantageously, a complexing agent of moderate complexing strength is able to provide mobilization and redistribution without undue leaching.

In many representative embodiments, a treatment strategy involves contacting the substrate with a fluid composition that is derived from ingredients including at least a liquid carrier comprising at least one complexing agent. Via an equilibrium, a portion of metal biocide in the substrate will tend to form a water soluble complex with the complexing agent. The treatment tends to cause the metal biocide in the substrate to exist in at least two phases. A first, liquid phase comprises complexed metal biocide dissolved in the liquid carrier, and at least a portion of the remaining metal biocide is incorporated into a second, separate phase. The metal biocide in the second phase generally is in a form that is less soluble than the complexed biocide. Consequently, the metal biocide might be present in the second phase as a constituent of precipitated and/or dispersed particles fixed or otherwise distributed in the substrate. The complexing agent is selected so that at least a portion of the complexed metal biocide in the first phase is in equilibrium with at least a portion of the metal biocide in the second phase.

Without wishing to be bound, it is believed that the ability of treatment compositions to modify the distribution of metal biocide within a substrate is due at least in part to equilibrium effects between the complexing agent and the metal biocide. Specifically, it is believed that an equilibrium occurs dynamically in the substrate between the complexing agent and the metal biocide. At any one point in time, a portion of the metal biocide is in water-soluble, complexed form(s), while the remainder tends to be in insoluble state(s) per the equilibrium. At such a point in time, the current dissolved portion is relatively mobile and, consequently, is more able to move through the substrate for redistribution. Subsequently, as part of the equilibrium, a differing portion of biocide will be complexed and mobilized. Over time, it is believed that at least significant portions of the available metal biocide in contact with the post-treatment composition participates in equilibrium reactions such that differing portions of the metal biocide are continuously being complexed and then precipitating into one or more insoluble states and vice versa. Over time, a much greater portion of the metal biocide than just that which can be bound by the complexing agent at one point in time is dissolved and mobile as a practical matter. As successive portions are dissolved and mobilized, the metal biocide is redistributed more uniformly and more thoroughly at least in those regions into which the post-treatment composition has penetrated.

The complex stability constant, $K_1$, is useful for evaluating the degree to which a metal or metal containing species can participate in equilibrium with a complexed counterpart of the metal or metal containing species. In the practice of the present invention, the value of this constant indicates whether the complexing agent is of a kind that will promote the desired mobilization and redistribution. Generally, the complex stability constant $K_1$ is given by the expression $$K_1 = \log([LM]/[L][M]),$$

where L is the complexing agent, M is the metal or metal containing species in equilibrium with the complexed metal, and LM is the complexed metal. Generally, a complexing agent binds more strongly to the metal as $K_1$ increases. If $K_1$ is too high, the complexing agent may bind to the metal too strongly and may not participate in either the desired equilibrium reaction(s) to the degree that might be desired or in interactions with the substrate. When the $K_1$ is too high, the tendency of the complex to leach also tends to increase. On the other hand, if the $K_1$ is too low, then solubility of the complex and/or transport into the substrate might be inhibited to a larger degree than might be desired. Balancing these concerns, the complexing agent and the metal biocide have a complex stability constant $K_1$ at 25° C. in the range from about 2.5 to about 6.5, preferably from about 2.5 to about 6, more preferably from about 3 to about 5.5, and even more preferably from about 3.5 to about 5.5. Note that the present invention does not exclude the use of complexing agents with $K_1$ values outside these ranges so long as at least a majority on a molar basis, preferably at least 80% on a molar basis, and more preferably at least about 95% on a molar basis of the complexing agent(s) respectively have a $K_1$ within these ranges.

In the practice of the present invention, complex stability constants may be obtained from the NIST Critically Selected Stability Constants of Metal Complexes Database, which may be updated from time to time. In some circumstances, more than one value may be provided for some constants for some particular metal-ligand combinations. In such circumstances, the constant used herein may be determined as an average of the values listed so long as the listed values are within 15% of each other. If three or more values are listed, any value more than two standard deviations away from the average may be discarded, and then an average is re-computed for the remaining listed values. If all values are more than two standard deviations from the average, then the average computed without discarding any entries may be used. In the event that a constant of interest is not listed in the NIST database, then the value for such constant may be obtained from the IUPAC Stability Constants Database (SC-Database) using the same protocol for computing an average value as described herein for the NIST database when more than one value for the constant is listed in the IUPAC database.

A wide variety of complexing agents may be used in the practice of the present invention. These include organic acids such as aspartic acid, citric acid, and oxalic acid; ammonia; polyamine functional compounds such as ethylenediamine; nitrogen-containing alcohols such as alkanolamines; combinations of these and the like. Examples of alkanolamines include monoethanolamine (MEA); isopropanolamine; 1-1- or 1,2-diaminoethanol; diethanolamine; dimethylethanolamine; triethanolamine (TEA); aminoethylethanolamine; combinations of these; and the like. The alkanolamines are presently preferred in complexes with copper. MEA, TEA, and mixtures of these are particularly preferred. The constant $K_1$ associated with MEA and $Cu^{+2}$ is about 4.5. MEA works very well in wood preservatives with copper because the $K_1$ value is quite suitable. Similarly, the combination of TEA and copper have a suitable $K_1$ of about 4.0. In contrast, the combination of EDA and copper has a $K_1=10$ and is much less desirable in this application, particularly if EDA is used alone as the only complexing agent, as EDA binds to copper very strongly. i.e., more than 100,000 times as strongly as MEA.

In those embodiments in which a mixture of alkanolamines such as MEA to TEA are used, the molar ratio of MEA to TEA can vary over a wide range. For instance, the molar ratio of MEA to TEA may be in the range from 1:100 to 100:1, preferably 1:10 to 50:1 more preferably 1:2 to 25:1. In one illustrative embodiment, a molar ratio of 10:1 would be suitable.

In those embodiments in which additional metal biocide is included as a constituent of the post-treatment composition, it is desirable that the molar ratio of MEA to TEA is greater than 1 based upon several factors. For example, the molecular weight of TEA is higher than the molecular weight of MEA. For concentrated embodiments, using too much TEA might make the solution more viscous than might be desired. Hence, using more MEA helps to provide more desired viscosity characteristics. MEA also provides complexes with more desirable performance characteristics in the present context. However, using at least some TEA remains desirable. TEA is less basic than MEA and helps to moderate the pH of the resultant solutions. TEA is also less volatile.

The amount(s) of complexing agent(s) incorporated into the post-treatment compositions of the present invention may vary over a wide range. Generally, using too much complexing agent can lead to too much leaching of both metal biocide that is redistributed from other parts of the substrate as well as with respect to metal biocide applied to replenish the substrate as a constituent of the post-treatment composition. On the other hand, using too little complexing agent may fail to accomplish adequate mobilization of metal biocide to accomplish redistribution and/or replenishment within a reasonable time. As general guidelines, post-treatment compositions of the present invention may include from about 0.01 to about 5 weight percent, preferably 0.1 to about 3 weight percent, and more preferably from about 0.25 to about 2.5 weight percent of complexing agent(s) based upon the total weight of the post-treatment composition.

In embodiments in which a post-treatment composition includes one or more metal biocide(s) such as Cu, the molar ratio of the total complexing agent to the moles of metal(s) from the metal biocide(s) is generally is in the range from about 3:1 to about 1000:1, preferably about 3:1 to about 100:1.

Often, the liquid carrier of the post-treatment compositions are aqueous or partially aqueous. In many illustrative embodiments, the liquid carrier is at least 50 weight percent, preferably at least 75 weight percent, and more preferably at least 90 weight percent water. In addition to water, the liquid carrier of the preservative compositions may further include one or more optional solvents to help dissolve or disperse composition ingredients. Such additional solvents are either fully miscible with water or are used in sparing amounts when it is desired to avoid phase separation among the components. Examples of such optional solvents include alcohols such as ethanol and isopropanol, tetrahydrofuran, acetonitrile, combinations of these, and the like.

In addition to the liquid carrier and one or more complexing agents, the post-treatment compositions may further include one or more other optional ingredients in order to enhance manufacture, use, performance, or the like. As one option, post-treatment compositions of the present invention may include one or more metal biocides such as those listed above. The metal biocide(s) used in the post-treatment composition may be the same or different than the metal biocide already present in the substrate at the time of the post-treatment. A preferred metal biocide for use in the post-treatment compositions also is copper. Due to present regulatory requirements, and just as was the case with the preservative compositions used to impregnate the substrates initially, it is desirable to limit or avoid the use of Cr and/or As in the post-treatment compositions for residential applications.

The metal biocide may be present in soluble and/or insoluble form(s), but preferably is present in soluble form(s) such that the post-treatment composition is homogeneous (i.e., a single phase composition) or is present in both soluble and insoluble forms in equilibrium such that the post-treatment composition is a hybrid composition as described in Assignee's co-pending application U.S. Ser. No. 61/069,484, filed Mar. 14, 2008, by Keen et al., HYBRID STRATEGIES FOR REDUCING LEACHING OF METAL BIOCIDES FROM BIODEGRADABLE SUBSTRATES, the entirety of which is incorporated herein by reference for all purposes. Homogeneous compositions are preferred. With respect to the relatively insoluble metal biocide portion of the hybrid preservative composition, one or more metal biocide(s) may be initially supplied as ingredient(s) to be incorporated into the composition, or a component of the composition, in a wide variety of solid forms. Alternatively, the relatively insoluble metal biocide material may be obtained from ingredients (s) that form insoluble material in situ. These in situ reactions may be the same or different than the equilibrium reactions between the relatively insoluble material and the soluble material. The solid material, and/or resultant solid material if formed in situ, may be in the form of precipitates, particles, pellets, granules, fibers, composites, combinations of these, and the like. Often, the solid material is supplied in the form of particles as these are economical to obtain or make, easy to handle in formulating and applying compositions, and/or readily form in situ.

With respect to selecting particles for initially formulating hybrid compositions of the present invention, a very wide range of particle sizes would be suitable in the practice of the present invention. Generally, any particle sizes that are reasonably compatible with desired manufacturing, packaging, and/or use techniques are suitable. More desirably, particles are small enough to penetrate at least into the largest pores of the substrate initially, after which equilibrium effects as discussed above can help the material achieve a more thorough and uniform substrate penetration. As general guidelines, particle size can be about 2 mm or less, desirably in a range from about $10^{-6}$ mm to 2 mm, more desirably from about $10^{-5}$ mm to about 0.1 mm, even more desirably from about $10^{-4}$ mm to about 0.05 mm.

The term particle size refers to the volume based particle size. For a specific particle, the volume based particle size is the diameter of a sphere having the same volume as such particle. For a particle sample comprising a population of particles, the volume based particle size is the mean volume based particle size of the volume distribution of the sample as determined using laser diffraction techniques, such as by using any of the laser diffraction particle size analyzers commercially available from Beckman Coulter (these include the LS™ 13 320 Series laser diffraction particle size analyzers, the LS™ 2 Series laser diffraction particle size analyzers which are preferred, and the LS™ 100Q laser diffraction particle size analyzer) for particle samples in which at least 90 weight percent of the particles have an average volume based particle size in the range from 0.4 micrometers to 2 mm. For smaller particle sizes, x-ray diffraction techniques may be used, optionally equipped with a synchrotron source for particle sizes in the range from 0.003 micrometers to about 0.5 micrometers.

The particles can have any kind of particle size distribution (s). For instance, in addition to some particle ingredients of the invention having normal distributions, other particulate ingredients used to formulate hybrid compositions may include particle size characteristics with two or more size distribution peaks. Combinations of particle ingredients with different or similar distribution profiles may also be used. For instance, the particulate ingredients may be a blend derived from relatively coarse grains and relatively fine grains. This might be desirable in embodiments where two different metal biocides are being used. Although supplying the particles in an extremely finely divided form to facilitate substrate penetration is not required, the particles optionally may be mechanically, physically, chemically, or otherwise sized to provide them in an alternatively desired particle size configuration.

The relatively insoluble material containing one or more metal biocides initially may be in a wide variety of chemical forms that are reactive with the relatively soluble material via equilibrium reaction(s). In some embodiments, the relatively insoluble material may be ionic or nonionic. In some embodiments, the relatively insoluble material may be crystalline, partially crystalline, or amorphous. When the relatively soluble material includes one or more complexes of one or more metal biocides, illustrative insoluble forms include pure metals, metal alloys, intermetallic compositions, composites, oxides, oxyhalides, oxyhydroxides, hydroxides, carbonates, formates, basic carbonates, quinolates, carbamates, omadines, borates, other salts, combinations of these, and the like.

For example, in the case of copper, suitable relatively insoluble material reactive with complexing agents include cuprous oxide, cupric oxide, copper hydroxide, copper carbonate, copper basic carbonate, copper oxychloride, copper-8-hydroxyquinolate, copper dimethyldithiocarbamate, copper omadine, copper borate, copper metal byproducts, copper sulfate, copper fluoroborate, copper fluoride, copper formate, copper acetate, copper bromide, copper iodide, copper basic phosphate, copper basic phosphor-sulfate, copper basic nitrate, combinations of these, and the like. Copper basic carbonate, which may be represented by the simplified formula $Cu(OH)_2$—$CuCO_3$, is an example of one preferred source of relatively insoluble copper.

In preferred embodiments, the relatively soluble state of the metal biocide is in the form of a metal complex. The complex is easily obtained by reacting a suitable source of the metal biocide with one or more complexing agents in an aqueous reagent. Suitable metal biocide sources include the sources identified above for insoluble forms of the metal biocide. The complexing agent helps dissolve and/or distribute the complexed metal biocide or metal biocide-containing species. The use of the complexing agent may be desirable even when the Cu is supplied from a highly water-soluble source inasmuch as the resultant complexes are more resistant to precipitation and/or settling during manufacture, packaging, storage, dilution with various water supplies, preserving treatments, and/or other handling. The use of complexing agents is a straightforward, economic way to dissolve the metal biocides in aqueous media and to facilitate a more uniform distribution of the metal biocide in the substrate.

In calculating the weight percent metal biocides(s) incorporated into a composition throughout this specification, only the weight of the metal(s) per se is/are used to make the calculation without inclusion of the weight of other species that might be included with the metal(s) in the metal source (s). For example, if 15 grams of copper basic carbonate deemed to have the simplified formula $Cu(OH)_2$—$CuCO_3$ is incorporated into a composition whose total weight is 100 g including the added copper basic carbonate, then the weight percent of copper in this composition is 8.6 weight percent.

Agent(s) that help protect against leaching are also desirable, optional ingredient(s) of the post-treatment composition. A problem with soluble or easily dispersed forms of metal biocides is that these may tend to more readily leach from treated, biodegradable substrates when exposed to rain or other sources of water. Advantageously incorporating a leaching-reducing agent into the post-treatment composition can help protect against leaching. Particularly preferred leaching-reducing agents are described in Assignee's copending U.S. Provisional Application having U.S. Ser. No. 61/007,614, filed Dec. 13, 2007, in the names of Kimberly S. Hayson, William C. Hoffman, Albert F. Joseph, Brian T. Keen for STRATEGIES FOR REDUCING LEACHING OF WATER-SOLUBLE METAL BIOCIDES FROM TREATED WOOD PRODUCTS and the entirety of which application is incorporated herein by reference for all purposes.

According to this co-pending application and as used herein, preferred agents that reduce leaching of metal biocides are water soluble, are substantially nonionic in aqueous media, have a molecular weight (or a weight average molecular weight if the agent is present as a population distribution) greater than about 100, and have a vapor pressure less than that of water. Preferred embodiments of these agents described further below not only protect against leaching but also help to protect substrates against degradation due to ultraviolet exposure from the sun. These agents also help improve the dimensional stability of substrates.

As used herein, water soluble with respect to the leaching-reducing agent means that a homogeneous solution may be prepared by dissolving 0.5 grams, 1.0 grams in some embodiments, and even 2.0 grams in some embodiments, of the agent(s) in 100 ml of distilled water, and then, when the resultant solution is stored at 25° C., at least 90% of the agent(s) remain in solution for at least two hours. When a single agent is to be used, the single agent to be used is dissolved in the water to assess water solubility. When a mixture of two or more agents are to be used in the treatment solution, an appropriate sample of the mixture in the intended proportions to be used is dissolved in the water to assess solubility.

Generally, molecular weight is one factor that impacts the ability of an agent to protect against leaching. If the molecular weight is too low, e.g., below about 100, or even below about 80, a material may not protect against leaching at all and may even increase leaching. On the other hand, agents of the invention having a molecular weight above about 100 tend to provide greater leaching protection. Indeed, leaching protection tends to increase as molecular weight, or weight average molecular weight as appropriate, increases. This means that agents with higher molecular weights generally can be used at lower usage rates to provide comparable or better leaching protection than agents with lower molecular weight. Accordingly, a leaching reducing agent of the present invention desirably has a molecular weight (or weight average molecular weight, as appropriate) of at least 100, more desirably at least about 150, even more desirably at least about 200, and even more desirably at least about 500.

However, there tends to be a maximum molecular weight beyond which use of an agent may become impractical. For instance, if the agent is too large, the impregnation solution may gel or otherwise be too viscous and/or impregnation may become unduly difficult. Accordingly, it is preferred that an agent of the present invention has a molecular weight (or weight average molecular weight, if appropriate) of no more than about 100,000, desirably no more than about 50,000, more desirably no more than about 30,000.

The leaching-reducing agent of the present invention also has a vapor pressure less than that of water at standard temperature. This helps ensure that the agent evaporates more slowly than water during a drying phase after impregnation, during the course of manufacture, and/or after an impregnated wood product is exposed to water (e.g., rain or the like) during its service life. In other words, the agent, as an organic phase, tends to concentrate relative to water as the relatively more volatile water evaporates faster. Without wishing to be bound, it is believed that the relatively concentrated organic phase, due to partition coefficient effects, helps to reduce the propensity for complexed metal biocide to be dissolved in the water that may be present. This enhances the ability of the wood to retain the metal biocide relative to the water, reducing leaching that might otherwise occur. Stated schematically, both the wood and water compete for the metal biocide. Leaching may have a greater tendency to occur when water is a relatively stronger competitor. However, in the presence of the additives of the present invention, the biodegradable substrates are relatively stronger competitors than they would be in the absence of the additives, resulting in less leaching.

Desirably, preferred leaching-reducing agents of the present invention have a vapor pressure of less than 15 mmHg, preferably less than 10 mmHg, more preferably less than 1 mmHg, and even less than 0.1 mmHg at 25° C. By way of comparison, water has a vapor pressure of about 24 mmHg at 25° C. Some embodiments of the leaching-reducing agents of the present invention by themselves may be in the form of solids at room temperature. Such materials tend to sublime to some very minor degree, but may be viewed as having a negligible vapor pressure well below 0.1 mmHg at 25° C. for purposes of the present invention.

Substantially nonionic leaching-reducing agents of the present invention may tend to include some nonionic and/or ionic impurities as prepared or as obtained from commercial sources, as the case may be. Taking into account the potential presence of such impurities, preferred substantially nonionic leaching-reducing agents of the present invention are those containing less than 5 weight percent, preferably less than 2 weight percent, and more preferably less than 0.5 weight percent of nonionic and/or ionic impurities. However, so long as at least one such substantially nonionic substance is used to help protect against leaching, preservative compositions optionally may include one or more ionic species if desired for a variety of purposes. Examples of such ionic species include metal salts, quaternary ammonium salts, other inorganic and/or organic salts, combinations of these, and the like, such as the polymeric quaternary ammonium borates containing PEG blocks described in U.S. Pat. Nos. 5,304,237 and 5,874,025.

In addition to the combination of characteristics mentioned above, preferred leaching reducing agents may also have one or more additional characteristics, either singly or in combination, to further enhance leaching protection. For instance, in some embodiments, it is preferred that the leaching reducing agents are substantially neutral. As used herein, "substantially neutral" means that a solution of 0.5 grams, preferably 1.0 grams, or more preferably 2.0 grams, of the agent or agent(s) dissolved in 100 ml of distilled water has a pH in the range of from about 4 to about 10, preferably from about 5 to about 9, more preferably about 6 to about 8 at 25° C. When a single agent is to be used, the single agent to be used is dissolved in the water to assess pH characteristics. When a mixture of two or more agents are to be used, an appropriate sample of the mixture in the intended proportions to be used is dissolved in the water to assess pH characteristics.

As another optional, desirable characteristic, preferred leaching-reducing agents are those including at least about 4 weight percent, more preferably at least about 4 to about 55 weight percent, and even more preferably at least about 20 to about 45 weight percent oxygen. Examples of these preferred agents include (poly)ethers and/or nonionic surfactants including one or more oxyalkylene units in the backbone and/or as substituents of the molecule. As used herein, the term "(poly)" with respect to an ether indicates that the ether may have one or more oxyalkylene units. The term "poly" without parentheses indicates that the material includes two or more oxyalkylene repeating units, which may be the same or different. In some embodiments, the ingredients that help to improve leaching resistance comprise a combination of a (poly)ether and a nonionic surfactant incorporating one or more of such oxyalkylene groups, respectively. Representative embodiments of (poly)ethers of the present invention comprise one or more linear, branched, and/or cyclic, divalent oxyalkylene repeating units, or combinations of these. The (poly)ethers may be homopolymers or copolymers of two or more copolymerizable materials. If made from two or more copolymerizable materials, the different materials may be incorporated into the (poly)ether randomly or in blocks.

In the practice of the present invention, a divalent, oxyalkylene unit generally has the formula —RO—, wherein R is any straight, branched, or cyclic alkylene or aralkylene, divalent moiety often including from 1 to 10, desirably 1 to 5, more desirably 1 to 3 carbon atoms. Repeating units with larger numbers of carbon atoms may be incorporated into the (poly)ether if desired. However, if the units include too many carbon atoms, or if the (poly)ether includes too large a percentage of repeating units having a relatively large number of carbon atoms, or if the agent is too large, the water solubility of and/or leaching protection provided by the (poly)ether may suffer. Examples include —CH$_2$O—, —CH$_2$CH$_2$O—, —CH$_2$CH$_2$CH$_2$O—, —CH$_2$CH(CH$_3$)O—, —CH(CH$_3$)CH$_2$O—, —CH$_2$CH(CH$_2$CH$_3$)O—, —CH(CH$_2$CH$_3$)CH$_2$O—, —CH$_2$CH(CH$_3$)CH$_2$O—, —CH(CH$_3$)CH$_2$CH$_2$O—, —CH$_2$CH(CH$_2$CH$_3$)CH$_2$O—, —CH(CH$_2$CH$_3$)CH$_2$CH$_2$O—, —CH$_2$CH$_2$CH(CH$_2$CH$_3$)O—, additional variations in which more than one substituent of the oxyalkylene backbone is an alkyl moiety, combinations of these, and the like. The (poly)ethers desirably have terminal groups selected from H; linear, branched or cyclic alkyl of 1 to 12 carbon atoms; alkoxy of 1 to 12 carbon atoms; and combinations of these. Often, a commercially available product will include more than one kind of —RO— moiety within individual molecules in those embodiments when the number of —RO— repeating units is greater than one on average. Additionally, commercially available products may include a population distribution of different (poly)ether molecules.

Suitable (poly)ethers are often commercially available as a mixture containing a distribution of (poly)ether polymers with varying number of repeating units and a corresponding variation in molecular weight. Preferred (poly)ether populations of this sort generally may have an average of at least two and preferably from about 1 to about 3000 of these divalent, oxyalkylene repeating units. In more preferred embodiments, the (poly)ethers have a sufficient number of these repeating units such that the (poly)ether material has a weight average molecular weight in the range from at least about 100 to about 50,000, preferably from about 300 to about 30,000, more preferably from about 500 to about 20,000.

The (poly)ether preferably includes at least one (poly)ethylene glycol (PEG). A PEG is a linear (poly)ether polymer incorporating two or more oxyethylene (EO) repeating units and may be represented by the formula $$R^1O\text{---}(CH_2CH_2O)_n\text{---}R^2$$

wherein each of $R^1$ and $R^2$ independently is H or straight, branched, or cyclic alkyl, preferably H or alkyl of 1 to 12 carbon atoms, often 1 to 3 carbon atoms; and n is 1 to 3000 and preferably is a number such that the PEG has a weight average molecular weight in the range of from at least about 100 to about 50,000, preferably from about 300 to about 30,000, more preferably from about 500 to about 20,000.

Another class of (poly)ether materials that would be useful in the practice of the present invention are copolymers at least incorporating one or more oxyethylene and one or more oxypropylene (PO) repeating units according to the formula $$R^3O\text{---}(CH(CH_3)CH_2O)_m\text{---}(CH_2CH_2O)_n\text{---}R^4$$

wherein each of $R^3$ and $R^4$ independently is H or straight, branched, or cyclic alkyl, preferably H or alkyl of 1 to 12 carbon atoms, often 1 to 3 carbon atoms; m is 1 to 3000; n is 1 to 3000; and m+n preferably is a number such that the PEG has a weight average molecular weight in the range of from at least about 100 to about 50,000, preferably from about 300 to about 30,000, more preferably from about 500 to about 20,000. Desirably, the ratio of m to n may be in the range from about 1:4 to about 4:1, preferably about 1:1.5 to 1.5:1. In this formula, any other isomer(s) of oxypropylene may be present.

Optionally, in addition to the oxyalkylene units, any (poly) ethers used in the practice of the present invention may further incorporate up to 70 weight percent, desirably up to 25 weight percent, more desirably up to 10 weight percent, and even more desirably up to 2 weight percent of other copolymerizable materials. Examples of such other materials are monomers that include free radically polymerizable functionality such as carbon-carbon double bonds. These materials include monomers such as olefins (ethylene, propylene, butadiene, etc.), (meth)acrylates, styrene-type materials, combinations of these, and the like.

Methods for preparing (poly)ether polymers, including PEG polymers and copolymers of EO and PO are known to those skilled in the art. In addition, the starting materials, often including EO, PO, butanol, glycerol, and hydrogen, are commercially available.

Specific examples of commercially available (poly)ether materials are the CARBOWAX PEG 8000 (weight average molecular weight of about 8000) and the CARBOWAX PEG 1000 (weight average molecular weight of about 1000) polyethylene glycol products commercially available from The Dow Chemical Co. Other examples include glycol ethers such as butoxy triglycol, tripropylene glycol butyl ether, tetraethylene glycol, as well as the glycol ethers available under the trade designation CELLOSOLVE (e.g., Butyl CELLOSOLVE Solvent and Hexyl CELLOSOLVE Solvent) from The Dow Chemical Co.

The amount of the leaching reducing agent incorporated into the preservative composition may vary over a wide range. Representative embodiments may include from about 0.01 to about 200, desirably 0.5 to about 50 parts by weight of the leaching reducing agent per one part by weight of the metal biocide. As is the case above in calculating the weight percent of metal biocide in the composition, the relative parts by weight of the leaching reducing agent relative to the metal(s) is based upon the weight(s) of the metal(s) themselves without inclusion of the weight of other species that might be included with the metal(s) in the metal source(s).

The leaching-reducing agent may also be in the form of, or further include in combination with another agent, one or more nonionic surfactants to help promote leaching resistance. In particular, embodiments of preservative compositions including both (poly)ether and a nonionic surfactant demonstrate excellent leaching resistance, even when only a relative minor proportion of the nonionic surfactant is used relative to the (poly)ether. Nonionic surfactants refer to compounds having at least one hydrophilic moiety coupled to at least one hydrophobic moiety wherein the surfactant carries no discrete cationic or anionic charge when dissolved or dispersed in the preservative composition.

A wide range of nonionic surfactants may be used. In preferred embodiments, the hydrophilicity of the nonionic surfactant is provided by a polyoxyalkylene moiety of the formula —$(R^5O)_w$— wherein $R^5$ is alkylene of 1 to 5 carbon atoms, particularly —$CH_2$— (methylene), —$CH_2CH_2$— (ethylene), propylene, isopropylene, butylene, or isobutylene; and w is often 1 to about 100. $R^5$ preferably is ethylene, propylene, or isopropylene. This polyoxyalkylene moiety is capable of strong hydrogen bonding with water, providing the desired hydrophilic characteristics.

The hydrophobicity of the nonionic surfactant is generally provided via a nonpolar moiety coupled to the hydrophilic moiety. Nonpolar desirably means that the moiety includes at least 6 carbon atoms to 100 carbon atoms, preferably at least 10 carbon atoms to 100 carbon atoms; and that there are no more than 2 hetero atoms such as O, S, N, P or the like per 6 carbon atoms, preferably per 10 carbon atoms, more preferably per 15 carbon atoms. In representative embodiments, the hydrophobic moiety is linear, straight, or cyclic alkyl, aryl, aralkyl; or alcohol. Preferred hydroxyl moieties are secondary.

A representative embodiment of a nonionic surfactant is an adduct of an EO or an EO/PO (poly)ether and an alcohol, desirably a secondary alcohol. Such an adduct may have the following formula:

$$R^6O\text{---}(R^7O)_p\text{---}R^9$$

wherein $R^6$ is a straight, branched, or linear nonpolar group, cyclic or aryl of 10 to 100, preferably 10 to 50 carbon atoms; each $R^7$ is independently an alkylene moiety of 1 to 4 carbon atoms, preferably 2 to 3 carbon atoms, and $R^9$ is H or a monovalent moiety comprising 1 to 20 carbon atoms, preferably 1 to 10 carbon atoms and may be non-aryl or aryl; and p is 1 to 200. Particularly preferred embodiments of such an adduct independently have the formulae $$R^{10}O\text{---}(CH_2CH_2O)_k\text{---}(CH(CH_3)CH_2O)_q\text{---}H$$

$$R^{10}O\text{---}(CH_2CH_2O)_k\text{---}(CH_2CH(CH_3)O)_q\text{---}H$$

$$R^{10}O\text{---}(CH_2CH_2O)_k\text{---}(CH(CH_2CH_3)CH_2O)_q\text{---}H$$

$$R^{10}O\text{---}(CH_2CH_2O)_k\text{---}(CH_2CH(CH_2CH_3)O)_q\text{---}H$$

wherein each $R^{10}$ independently is a hydrocarbon group of 10 to 50 carbon atoms; each k independently is 0 to 80; each q independently is 0 to 40 with the proviso that k+q is greater than or equal to 1. Also included are variants in which an adduct includes a mixture if branched oxyalkylene units contributing towards the total number of q repeating units or variants of these branched oxyalkylene units including two or more pendant alkyl substituents from one or more carbon atoms also contributing to the total number of q repeating units. Often, a commercially available product will include a population distribution of such adducts such that the values for molecular weight, k and q may be expressed as an average.

In such mixtures, molecular weight refers to weight average molecular weight throughout this specification unless otherwise expressly noted.

Any amount of nonionic surfactant that is effective to help reduce leaching may be used in the preservative composition. It has been found, however, that leaching resistance is enhanced if the weight ratio of the (poly)ether to the nonionic surfactant is greater than about 1. Accordingly, the weight ratio of the (poly)ether to the nonionic surfactant is greater than 1:1, preferably from about 2:1 to about 50:1, more preferably from about 3:1 to about 20:1.

Other optional ingredients may also be beneficially used in the post-treatment composition in accordance with conventional practices. In addition to one or more metal biocides, for instance, the post-treatment compositions may also include one or more additional co-biocides to provide a broader biocidal spectrum against microbes, fungi, pests, etc. Additional co-biocides may include one or more of fungicidal, insecticidal, moldicidal, bactericidal, algaecidal biocides, and/or the like such as those listed above with respect to use in the preservative compositions used to initially treat a substrate prior to a post treatment. Just as was the case above, particularly preferred co-biocides include quaternary ammonium salts and the azole materials, including triazoles and imidazoles. Benzalkonium chloride or carbonate is one preferred quaternary ammonium salt; didecyldimethylammonium chloride or carbonate is another commonly used quaternary ammonium salt. Exemplary azoles include tebuconazole and propiconazole.

Additionally, during the course of manufacture, if metal vessels may be used to prepare, transport, store, or otherwise contact the composition, the compositions may include a corrosion inhibitor. Boron containing inhibitors such as boric acid used in corrosion inhibiting amounts have been found to be suitable for this purpose. Other adjuvants include dispersants, emulsifiers, binders, fixatives, water repellants, coloring agents, antioxidants, ultraviolet stabilizers, emulsifiers, antistatic agents, dessicants; precipitation inhibitors; buffers; fire retardants; combinations of these, and the like used in accordance with conventional practices.

The compositions may be prepared according to a variety of methods. It is beneficial to first combine the metal source and the complexing agent at generally the desired concentration in water with mixing to form the metal complex. Then, additional ingredients may be combined with the complex in one or more stages. According to one mode of practice, the reaction to form the metal complex may be carried out below, at, or above room temperature. It may be desirable to avoid heating the reaction mixture too much to avoid thermal degradation of the complexing agent.

The post-treatment compositions may be prepared, stored, and/or shipped initially as one or more concentrates (e.g., one part or two part concentrates) if desired. The concentrate(s) can then be combined if more than one is used and diluted for treatment of biodegradable products. A wide range of concentration/dilution schedules may be used. For example, the concentrate may be at least 5, desirably 5 to 500, more desirably 5 to 50, and most desirably 10 to 25 times more concentrated than the diluted form of the composition that will be used to actually treat biodegradable products. At the time of dilution, a wide range of liquids can be used for dilution. Preferred dilution liquids include water and/or water miscible liquids. Water immiscible materials should be used sparingly so as to avoid phase separation. For economical reasons, using water by itself would be suitable in most instances. If the dilution water includes species that might induce undue precipitation of the metal biocide(s) or other ingredient(s) of the compositions, it may be desirable to treat the water prior to dilution. Representative examples of treatments include one or more of physical or chemical filtering, extraction, distillation, reverse osmosis, softening, other mass transfer techniques for removing impurities, and the like. Precipitation inhibitors may also be included in the composition, if desired.

Concentrates may be prepared in accordance with conventional methodologies, such as according to the methodology of AWPA Standard P5-02 (referring to standard P5 issued in 2002). The anti-leaching agent(s) may then be added to the concentrate at any time prior to, during, and/or after dilution to the final concentration that will be used to carry out the impregnation treatment. The agent(s) can be directly added to the concentrate or pre-dissolved in a suitable liquid carrier (often water) and then added to the concentrate. The anti-leaching agent(s) may be added quickly or slowly over a time period extending from ten seconds to 8 hours. Whether added quickly or slowly, the ingredients desirably are added with thorough mixing. Moderate heating may be used to help obtain a homogeneous composition. Because concentrates generally have long shelf-life, the concentrates can be stored for considerable periods of time before addition of the anti-leaching agent(s).

The post-treatment compositions of the present invention can be used to treat biodegradable products using a variety of application or impregnation methods. These include manual methods such as spraying, brushing, rolling, immersion, pouring processes such as curtain coating, and the like. These also include automated methods such as pressurized impregnation, alternating pressure impregnation, vacuum impregnation, double vacuum impregnation, and the like. For in-service substrates in the field, such as those that are incorporated into part of a structure such as a deck, dock, fence, post, or the like, spraying, brushing, or rolling the composition onto the substrate under ambient temperature and pressure is easy and economical. One or multiple applications of the post-treatment composition may be applied with each post-treatment event. If multiple coats are used, it may be desirable to let one coat dry before applying another.

In terms of timing, the post-treatment can occur at any time after initial impregnation of a substrate. Such treatments may occur promptly after the initial impregnation or years afterwards. For instance, when using heterogeneous or hybrid preservative compositions as initial impregnation treatments, a post-treatment of the present invention may be applied promptly after the initial impregnation in order to enhance the uniformity and penetration of the metal biocide into the substrate. A typical process like this might involve two or more impregnation stages in the factory before the finished substrate is made available for use. In a first stage, a metal biocide is incorporated into the substrate via impregnation with a suitable preservative composition. In a subsequent stage, the substrate can be contacted with a post-treatment composition to help modify distribution of metal biocide in the substrate. If factory conditions are available, the post-treatment may occur using pressures or vacuum conditions different from ambient to enhance penetration of the post-treatment composition into the substrate. Multiple post-treatments may be applied if desired at the factory.

For post-treatment of in-service substrates, the treatment can occur at any time after the substrate has been put into service. This can range from carrying out one or more treatment(s) on the same day that the substrate is put into service to carrying out one or more treatment(s) days, months, years, or even decades later. Desirably, a post-treatment is applied before the integrity of the substrate has been compromised too much by decay. As mentioned above, regular maintenance programs can be carried out so that substrates receive a post-treatment periodically to help avoid undue depletion of metal biocide in the substrate, particularly proximal to the substrate surfaces. At each scheduled post-treatment event, multiple coatings of the post-treatment may be applied. Often, one to three coats would be suitable, allowing each coat to dry before the next is applied. Such programs may contemplate treatments that occur periodically, such as quarterly, semiannually, annually, biannually, every three years, or so forth in a way that helps maintain the integrity of the substrate. Maintenance programs like this offer the potential to dramatically extend the service life of these substrates.

The ability to improve the distribution of biocide post-manufacture facilitates earlier, effective treatments using lower levels of biocide and/or lesser amounts of treating solutions. For instance, initial treatments of biodegradable substrates might use excess treatment solution and/or higher concentration of biocide in treatment solutions to accommodate concerns such as service life leaching and/or penetration in the substrate. The ability to carry out a subsequent treatment to accommodate leached material, to upgrade penetration, or for other purposes eases the need to use excessive initial treatment levels. In short, the practice of the present invention allows less treatment materials to be used for an initial treatment, increasing efficiency significantly for the initial manufacturer of treated substrates.

The various aspects of the present invention will now be described with respect to the following illustrative examples. In the following examples, all percentages are parts by weight unless otherwise expressly indicated.

Preparation of Block Samples

A typical commercial, 4 inch by 4 inch by 8 foot Southern Yellow Pine timber treated for in-ground use (AWPA UC4a, 0.40 pcf Alkaline Copper Quaternary Type D) was purchased from Lowes. About 1 foot was cut off each end of the timber, and then approximately several one inch cross sections were cut off each end of the board. The respective cross-sections were arranged and numbered according to where they were cut. The first set of 4 inch by 4 inch nominal (actual 3.5 inch by 3.5 inch) by 1 inch cross-sections were labeled as Blocks 1-21 and the second set were labeled Blocks 50-70.

Each Block cross-section showed areas with and without significant copper penetration as evidenced by the presence or absence of the characteristic green color of the copper amine complex. A substantial portion of the center regions contained no color indicating the absence of copper in these regions. The absence of copper in this area was verified by spray test (AWPA Standard A3-00-7) and by using Energy Dispersive Spectroscopy. Typically the copper biocide had penetrated about 1.5 cm to about 3 cm from the outer edges of the cross sections into the interior.

Example 1

Wicking on Pressure Treated Wood (No Painted Sides)

Seventy five grams of a solution containing 3% by weight MEA in water was added to two flat glass containers as a post-treatment composition. The depth of the solution in the containers was about ¼ inches. Blocks 17, 18, and 15 were used, and these blocks as tested in this Example also are referred to herein as Samples 1a, 1b, and 1c, respectively. Cross section #17 (Sample 1a) from above was set upright in one container to absorb the post-treatment composition against the grain (radially) and section #18 (Sample 1b) was laid down flat in the second container to absorb the post-treatment composition with the grain (tangentially). In both cases a glass capillary was placed under each end of the cross sections to insure full access of post-treatment composition to the bottom block surface. Cross section #15 (Sample 1c) was retained as a standard for comparison. Samples were allowed to wick overnight. In both cases, the post-treatment compositions were essentially totally absorbed. The cross sections were taken out of the glass containers and allowed to dry overnight at room temperature on an oven rack. A chisel was used to remove the same representative 2 cm by 4 cm section from block #17 (Sample 1a), block #18 (Sample 1b) and block #15 (Sample 1c-reference). All three samples were tested by A3-00-7 Method for Determining Penetration of Copper-Containing Preservations spray test and Energy Dispersive Spectroscopy. Both section #17 and section #18 showed the presence of copper on all external surfaces not shown in the standard section #15. Comparative examination of the interior wood surfaces of section #17 and #18 showed some penetration distribution of copper into untreated regions beyond that of the standard, section #15.

This shows that contact with the post-treatment composition facilitated redistribution of copper. This also shows both internal (through the wood) and external (through the solution) re-distribution of the copper biocide.

Example 2

Wicking with Varnished Sides (Sides Sealed)

The flat surfaces of sample Block cross sections were sealed with two coats of polyurethane varnish. Block Sections #52 (Sample 2a) and #53 (Sample 2b) were used for this test. Seventy five grams of a solution containing 3% MEA in water were added to two flat glass containers as a post-treatment composition. The depth in the containers was about ¼ inches deep. One section was placed upright in a container to absorb the solution against the grain (radially) without vacuum. A second section was placed in the other container and placed in a dessicator. The section sat upright to absorb the solution against the grain (radially). A vacuum of 250 mm Hg (±10 mm) was applied and maintained to the dessicator. Both samples were allowed to wick over the weekend. The post-treatment composition wicked up each of the blocks approximately 3-4 centimeters. A majority of the treatment composition was absorbed in both cases. Samples were taken out the vessels and allowed to dry overnight. The same representative 2 cm by 4 cm center section of the blocks was removed by using a chisel. A third block, Block Section #56 (Sample 2c-reference), was used as a reference standard. All three samples were tested by A3-00-7 spray Method for Determining Penetration of Copper-Containing Preservations. Sections #52 and #53 showed that the copper had moved approximately 2 cm further up the section into the untreated region compared to the standard. This again shows that contact with the post-treatment composition facilitated redistribution of copper.

Example 3

Post Surface Treatment

Sections #54 (Sample 3c-reference), #55 (Sample 3a) and #57 (Sample 3b) were selected for testing. Section 54 was laid flat on the bench. Section 55 was laid flat on the bench and sprayed with a solution containing 5% by weight MEA in water. Section #57 was laid flat and sprayed with a solution containing 20% by weight MEA in water. All samples were allowed to dry overnight. AWPA Standard A3-00-7 spray Method for Determining Penetration of Copper-Containing Preservations was used to determine if copper had distributed from the treated to the untreated areas. Test showed the center region of block #54 had no copper. However, the method detected copper in sections #55 and #57 where no copper was previously present. Also, the method detected more copper in Section #57 than in section #55. This again shows that contact with the post-treatment composition facilitated redistribution of copper.

Example 4

Promoting Improved Metal Biocide Penetration

The two cut faces of four 4 inch by 4 inch by 1 inch sections were sealed with polyurethane as in Example #2 (Samples 4a, 4b, 4c & 4d, respectively). Sample 4a was saved as a reference. Samples 4b through 4d were leached in water with agitation over night, then removed from the water and allowed to dry. The leaching was presumed to remove any unfixed or loosely bound metal biocide. Sample 4b was retained as a leached reference. The same representative outer edge of 4c and 4d were treated with a solution containing 5% by weight MEA in water and 20% by weight MEA in water, respectively. The post treatment compositions were applied twice by spraying. Care was taken to ensure all of the compositions were absorbed by the blocks with de minimis overspray. The same representative 2 mm by 2 mm surface section was taken from 4a, 4b, 4c and 4d for X-ray Photoelectron Spectroscopy (XPS) analysis. Samples 4a and 4b showed about 0.4% surface copper. Samples 4c and 4d showed 0.25% and 0.15% surface copper respectively. This result demonstrates that the post-treatment solution complexes the metal biocide and mobilizes it for redistribution in the wood.

Example 5

Demonstrating Post Treatment Compositions of the Present Invention Sufficient to Facilitate Mobilization, Penetration and Redistribution of the Metal Biocide Do Not Result in Undue Metal Biocide Leaching Preparation of Post Treating Solutions As shown in Table 1, various post-treatment solutions were made by dissolving the components listed in distilled water at the prescribed concentrations. In Table 1, MEA=monoethanol-amine, TEA=triethanolamine, TTEG=tetraethylene glycol, PEG=polyethylene glycol 8000 mol wt, and quat.=benzalkonium chloride, Fluka 12060.
Wood Blocks Approximately ¾ inch by ¾ inch by ¾ inch Micronized treated wood blocks ("ProWood Micro" as manufactured by Universal Forest Products (Grand Rapids, Michigan) were used for Examples A-H. Approximately ¾ inch by ¾ inch by 5/4 inch aged (treated in 2006) commercial ACQ treated pine wood blocks were used for the examples I through L. Wood chosen for all examples was of consistent grain and texture. Blocks were placed in a constant humidity chamber overnight prior to testing. The humidity was maintained between 50% to 60%.

Post-Treating of the Wood Blocks—Examples B-H and J-L.

Nine knot and defect free blocks were chosen for each experiment. The block weights had a standard deviation of ±0.2 grams. Blocks were weighed and placed on a drying rack. Sample A micronized blocks were used as a reference. Samples B through H were treated with the various post treatment compositions shown in Table 1 by placing nine blocks for each sample in the bottom of a 500 ml Erlenmeyer flask with side arm. A perforated flexible plastic weighing dish was wedged on top the blocks to keep them fixed at the bottom of the flask. A 250 ml pressure-equalizing addition funnel containing 200 ml of the post treatment composition was connected to the top of the Erlenmeyer flask. The flask side arm was connected to house vacuum that was set at 250 mmHg. The vacuum was applied for 20 minutes while being maintained at 250±5 mmHg. After 20 minutes the post treatment composition was added to the blocks. After all the solution was added the vacuum was turned off. The blocks were allowed to absorb the composition for 30 minutes. After 30 minutes the blocks were removed from the solution. Each side of each block was slightly dabbed on a paper towel to remove any excess liquid. Each block was then weighed and placed on a rack to dry. After each set of blocks sat overnight at room temperature, they were place in a forced air convection oven for 5 days with the temperature maintained at 35° C.±1° C. A container of distilled water was placed in the bottom of the oven to help control the rate of drying of the blocks. Examples J through L were conducted in a similar manner using the solutions and wood blocks designated.
Copper Leaching Testing After 5 days the blocks were removed from the oven. The 6 blocks with the closest absorbed weights were placed in a pint jar and 300 mL of distilled water added to determine copper leaching. The jars were placed on an oscillating shaker and agitated at 120 rpm for 22 hours.

After removing from the shaker, a sample of the leaching solution was filtered and ppm copper was determined by Inductively Coupled Plasma (ICP) analysis. The results of Examples A-H are shown in Table 1.

Copper leaching for examples the B through G post-treated samples was low and close to the un-posttreated standard A. Example H demonstrates using higher concentrations of complexing agent could lead to more copper leaching.

In addition, when split open the blocks of Examples B through H show a uniform green color, indicative of dispersed copper complex and presumably increased bio-efficacy of the copper. In comparison, large particles of un-dissolved copper basic carbonate are observed in the un-post treated blank, Example A.

TABLE 1

Copper Leaching Study: Post Treatment
of "ProWood Micro-Universal Forest Products
(Grand Rapids, Michigan)"

| | Post Treating Solution | Average Post Treating Solution Absorbed Per Block (g) | Cu Leaching PPM 22 hr |
|---|---|---|---|
| Example A | Un-post-treated Micronized Wood Blank | 0 | 5 |
| Example B | 1% MEA in Water | 4.1 | 7 |
| Example C | 1% TEA in Water | 4.1 | 2 |
| Example D | 0.5% MEA in Water | 4.1 | 4 |
| Example E | 0.5% MEA in Water + 3% PEG 8000 | 3.9 | 3 |
| Example F | 1.0% TEA in Water + 3% PEG 8000 + 0.10% quat. | 3.8 | 3 |
| Example G | 5% TTEG + 0.5% TEA | 4.1 | 3 |
| Example H | 3% MEA | 4.2 | 17 |

Samples I-L:

Samples I through L illustrate practice of the invention with ACQ treated pine Wood (after about 2 years from initial ACQ treatment). These examples were conducted in an analogous fashion to examples A-H except aged ACQ treated wood was used.

The results of the copper leaching are shown in Table 2. The copper leaching observed in examples J-L are comparable to the standard example 1. These results show post-treatment with typical compositions of the invention do not cause increased copper leaching relative to the standard.

TABLE 2

Copper Leaching Study: Post
Treatment of Aged ACQ Treated Wood

| | Treating Solution | Average Treating Solution Absorbed Per Block (g)* | Cu Leaching PPM 22 hr |
|---|---|---|---|
| Example I | Un-post-treated Aged ACQ Wood Blank | 0 | 20 |
| Example J | 0.5% MEA in Water | 4.2 | 22 |
| Example K | 0.5% TEA + 3% PEG 8000 + 0.1% quat in water | 4.4 | 19 |
| Example L | 1% MEA in Water | 4.3 | 25 |

Blocks for Examples I through L were ~3/4" by 3/4" by 5/4"!

What is claimed is:

1. A method of treating a biodegradable substrate, comprising the steps of:
    a) providing the biodegradable substrate, said substrate comprising (i) a first substrate region distal from a surface of the substrate, said first substrate region having a first concentration of a metal biocide; and (ii) a second substrate region proximal to the surface of the substrate, said second substrate region having a second concentration of metal biocide that is reduced relative to the first substrate region; and
    b) contacting the surface of the substrate with an aqueous, fluid composition comprising a complexing agent capable of forming a water-soluble metal complex with the metal biocide, said complexing agent and metal biocide having a complex stability constant $K_1$ in the range of from about 2.5 to about 6.5, said contact causing a portion of the metal biocide in the first substrate region to be redistributed to the second substrate region.

2. The method of claim 1, wherein the complex stability constant is in the range from about 3 to 5.5.

3. The method of claim 1, wherein the substrate is cellulosic.

4. The method of claim 1, wherein the metal biocide comprises Cu.

5. The method of claim 1, wherein the aqueous, fluid composition is free of at least one of As and Cr.

6. The method of claim 1, wherein the aqueous, fluid composition is homogeneous.

7. The method of claim 1, wherein the aqueous, fluid composition is heterogeneous.

8. The method of claim 1, wherein the complexing agent comprises an alkanolamine.

9. The method of claim 1, wherein the complexing agent comprises monoethanol amine.

10. The method of claim 1, wherein the complexing agent comprises triethanol amine.

11. The method of claim 1, wherein the complexing agent comprises monoethanol amine and triethanol amine.

12. The method of claim 11, wherein the monoethanol amine and triethanol amine are present at a molar ratio of monoethanol amine to triethanol amine in the range from 1:2 to 25:1.

13. The method of claim 11, wherein the monoethanol amine and triethanol amine are present at a molar ratio of monoethanol amine to triethanol amine that is greater than one.

14. The method of claim 1, wherein the aqueous, fluid composition further comprises a leaching reducing agent.

15. The method of claim 1, wherein the aqueous, fluid composition further comprises a (poly)ether.

16. The method of claim 1, wherein the aqueous, fluid composition further comprises a nonionic surfactant.

17. The method of claim 1, wherein the aqueous, fluid composition further comprises a poly(ether) and a nonionic surfactant.

18. A method of restoring a metal biocide content in a depleted region of an in-service, biodegradable substrate by redistributing a portion of a metal biocide from at least one other region of the substrate to the depleted region, comprising the step of contacting a surface of the substrate with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase.

19. A method of treating a biodegradable substrate, comprising the steps of:
   a) providing the biodegradable substrate, said substrate comprising (i) a first substrate region distal from a surface of the substrate, said first substrate region having a first concentration of a metal biocide; and (ii) a second substrate region proximal to the surface of the substrate, said second substrate region having a second concentration of metal biocide that is reduced relative to the first substrate region; and
   b) contacting the surface of the substrate with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase.

20. A method of treating a biodegradable substrate to modify a distribution of a metal biocide already incorporated into the substrate, comprising the steps of:
   a) providing the substrate, said substrate comprising a distribution of a metal biocide; and
   b) contacting the substrate with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase.

21. A multi-step treatment for distributing a metal biocide in a biodegradable substrate, comprising the steps of:
   a) incorporating a metal biocide into the biodegradable substrate; and
   b) after step (a), contacting the substrate with an aqueous, fluid composition comprising a complexing agent capable of forming a water-soluble metal complex with the metal biocide such that the metal biocide exists in at least two phases when the substrate is contacted with the fluid composition, at least one of said phases comprising a water-soluble complex of ingredients comprising the complexing agent and the metal biocide and a second phase comprising the metal biocide in a form that is less water soluble than the water-soluble complex, wherein at least a portion of the complex in the first phase is in an equilibrium with the metal biocide in the second phase.

* * * * *